(12) United States Patent
Maust et al.

(10) Patent No.: US 11,846,618 B2
(45) Date of Patent: *Dec. 19, 2023

(54) METHOD AND APPARATUS FOR AUTOMATICALLY MAINTAINING A DESIRED LEVEL OF OXYGEN IN A REFUGE

(71) Applicants: David E. Maust, Grantsville, MD (US); Kyle D. Maust, Frostburg, MD (US); Kyle Murray, Somerset, PA (US); Rob Albinger, Gibsonia, PA (US)

(72) Inventors: David E. Maust, Grantsville, MD (US); Kyle D. Maust, Frostburg, MD (US); Kyle Murray, Somerset, PA (US); Rob Albinger, Gibsonia, PA (US)

(73) Assignee: Strata Products Worldwide, LLC, Sandy Springs, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/499,840

(22) Filed: Oct. 12, 2021

(65) Prior Publication Data

US 2022/0032097 A1 Feb. 3, 2022

Related U.S. Application Data

(62) Division of application No. 15/708,929, filed on Sep. 19, 2017, now Pat. No. 11,150,229.

(60) Provisional application No. 62/400,415, filed on Sep. 27, 2016.

(51) Int. Cl.
*A62B 31/00* (2006.01)
*G01N 33/00* (2006.01)
(Continued)

(52) U.S. Cl.
CPC .......... *G01N 33/0036* (2013.01); *A62B 7/02* (2013.01); *A62B 9/006* (2013.01); *A62B 9/02* (2013.01);
(Continued)

(58) Field of Classification Search
CPC ........... A62B 13/00; A62B 31/00; A62B 7/02; A62B 9/006; A62B 9/02
See application file for complete search history.

(56) References Cited

U.S. PATENT DOCUMENTS 4,891,004 A * 1/1990 Ballard ................... F23N 5/203
236/11
4,901,538 A * 2/1990 Anthony ................. F25D 15/00
62/263

(Continued)

*Primary Examiner* — Ko-Wei Lin
(74) *Attorney, Agent, or Firm* — Ansel M. Schwartz

(57) ABSTRACT

An apparatus for controlling a level of oxygen in a closed environment from an oxygen supply having an oxygen sensor for detecting the level of oxygen in the closed environment. The apparatus has a plurality of relays in communication with the sensor. The apparatus has a valve in communication with the relays and the oxygen supply which is automatically opened with the relays without human interaction, monitoring and adjustment to release oxygen from the oxygen supply into the environment when the level of oxygen in the environment goes below a first predetermined level and which is automatically closed with the relays without human interaction, monitoring and adjustment to stop oxygen from being released from the oxygen supply into the environment when the level of oxygen in the environment goes above a second predetermined level. A method for controlling a level of oxygen in a closed environment from an oxygen supply. A refuge chamber.

13 Claims, 2 Drawing Sheets

(51) Int. Cl.
*A62B 9/02* (2006.01)
*E04H 9/00* (2006.01)
*A62B 9/00* (2006.01)
*G05D 11/13* (2006.01)
*A62B 7/02* (2006.01)
*G05D 7/06* (2006.01)
*A62B 13/00* (2006.01)

(52) U.S. Cl.
CPC .............. *A62B 31/00* (2013.01); *E04H 9/00* (2013.01); *G01N 33/0067* (2013.01); *G01N 33/0073* (2013.01); *G05D 7/0635* (2013.01); *G05D 11/138* (2013.01); *A62B 13/00* (2013.01)

(56) References Cited

U.S. PATENT DOCUMENTS

| | | | |
|---|---|---|---|
| 7,593,212 B1 * | 9/2009 | Toth | G05D 23/1902 361/160 |
| 7,940,188 B2 * | 5/2011 | Calio | G01N 1/24 73/863.03 |
| 8,123,142 B2 * | 2/2012 | Cislo | F24F 7/007 454/258 |
| 8,534,640 B2 * | 9/2013 | Winistoerfer | G05B 7/00 251/129.03 |
| 2008/0011245 A1 * | 1/2008 | Donnelly | F24H 9/2035 122/14.2 |
| 2008/0083545 A1 * | 4/2008 | Olson | G08B 17/02 169/61 |
| 2012/0073670 A1 * | 3/2012 | Lymberopoulos | F16K 31/42 137/2 |
| 2013/0153060 A1 * | 6/2013 | Barrett | F17D 1/00 137/551 |
| 2014/0076324 A1 * | 3/2014 | Han | A62B 13/00 128/205.26 |
| 2014/0349565 A1 * | 11/2014 | Flood | G08B 21/02 73/23.3 |
| 2015/0056905 A1 * | 2/2015 | Baek | A62B 18/02 128/204.21 |
| 2015/0099449 A1 * | 4/2015 | Chen | H05K 7/20736 454/184 |
| 2015/0375985 A1 * | 12/2015 | Presley | B67D 7/04 222/1 |

* cited by examiner

METHOD AND APPARATUS FOR AUTOMATICALLY MAINTAINING A DESIRED LEVEL OF OXYGEN IN A REFUGE

CROSS-REFERENCE TO RELATED APPLICATIONS

This is a divisional of U.S. patent application Ser. No. 15/708,929 filed Sep. 19, 2017, now U.S. Pat. No. 11,150,229, which is a nonprovisional of U.S. provisional patent application Ser. No. 62/400,415 filed Sep. 27, 2016, all of which are incorporated by reference herein.

FIELD OF THE INVENTION

The present invention is related to automatically maintaining a desired level of oxygen in a refuge. (As used herein, references to the "present invention" or "invention" relate to exemplary embodiments and not necessarily to every embodiment encompassed by the appended claims.) More specifically, the present invention is related to automatically maintaining a desired level of oxygen in a refuge, using an oxygen sensor to control a valve that releases oxygen from an oxygen supply without human interaction, monitoring and adjustment.

BACKGROUND OF THE INVENTION

This section is intended to introduce the reader to various aspects of the art that may be related to various aspects of the present invention. The following discussion is intended to provide information to facilitate a better understanding of the present invention. Accordingly, it should be understood that statements in the following discussion are to be read in this light, and not as admissions of prior art.

Human refuges, mining and otherwise, require human interaction to match the oxygen delivery to the actual oxygen consumption/level. In such instances, it is common for excess pressure that is created by delivering oxygen to the refuge, to be lost into the external atmosphere outside the refuge through pressure relief valves. What is needed is a technique for Oxygen delivery to the refuge which is controlled automatically and not dependent on human interaction, monitoring and adjustment in a refuge, thus better insuring a proper amount of oxygen is being delivered to the refuge, and less oxygen is wasted by being vented out of the refuge through pressure relief valves.

BRIEF SUMMARY OF THE INVENTION

The present invention provides for Oxygen delivery which is controlled automatically and not dependent on human interaction, monitoring and adjustment in a refuge, such as a refuge chamber or safety room.

The present invention pertains to an apparatus for controlling a level of oxygen in a closed environment from an oxygen supply. The apparatus comprises an oxygen sensor for detecting the level of oxygen in the closed environment. The apparatus comprises a plurality of relays whose operations is controlled by the level of oxygen detected by the sensor. The apparatus comprises a valve in communication with the relays and the oxygen supply which is automatically opened by the relays without human interaction, monitoring and adjustment to release oxygen from the oxygen supply into the environment when the level of oxygen in the environment goes below a first predetermined level and which is automatically closed by the relays without human interaction, monitoring and adjustment to stop oxygen from being released from the oxygen supply into the environment when the level of oxygen in the environment goes above a second predetermined level.

The present invention pertains to a method for controlling a level of oxygen in a closed environment from an oxygen supply. The method comprises the steps of detecting with an oxygen sensor the level of oxygen in the closed environment is below a first predetermined level. There is the step of automatically opening a plurality of relays whose operations is controlled by the level of oxygen detected by the sensor without human interaction, monitoring and adjustment a valve which is in communication with the sensor and the oxygen supply to release oxygen from the oxygen supply into the environment. There is the step of detecting with the oxygen sensor the level of oxygen in the closed environment is above a second predetermined level. There is the step of automatically closing with the plurality of relays without human interaction, monitoring and adjustment the valve to stop oxygen from being released from the oxygen supply into the environment.

The present invention pertains to a refuge chamber. The refuge chamber comprises an enclosure which provides a protected environment for at least one person to be in. The refuge chamber comprises an oxygen supply in communication with the enclosure. The refuge chamber comprises an apparatus disposed in the enclosure for automatically controlling the oxygen level in the enclosure without human interaction, monitoring or adjustment having an oxygen sensor, a valve connected to the oxygen supply with a quick release hose, and a plurality of relays in communication with the sensor that control when the valve is open or closed regarding release of oxygen by the valve from the oxygen supply. The refuge chamber comprises a manifold disposed in the enclosure to which the quick release hose can be connected if the apparatus stops operating so oxygen can continue to be released from the oxygen supply. The manifold providing manual control by the person of the oxygen level when the quick release hose is connected to the manifold.

BRIEF DESCRIPTION OF THE SEVERAL VIEWS OF THE DRAWING

In the accompanying drawings, the preferred embodiment of the invention and preferred methods of practicing the invention are illustrated in which.

DETAILED DESCRIPTION OF THE INVENTION

Figure 1:
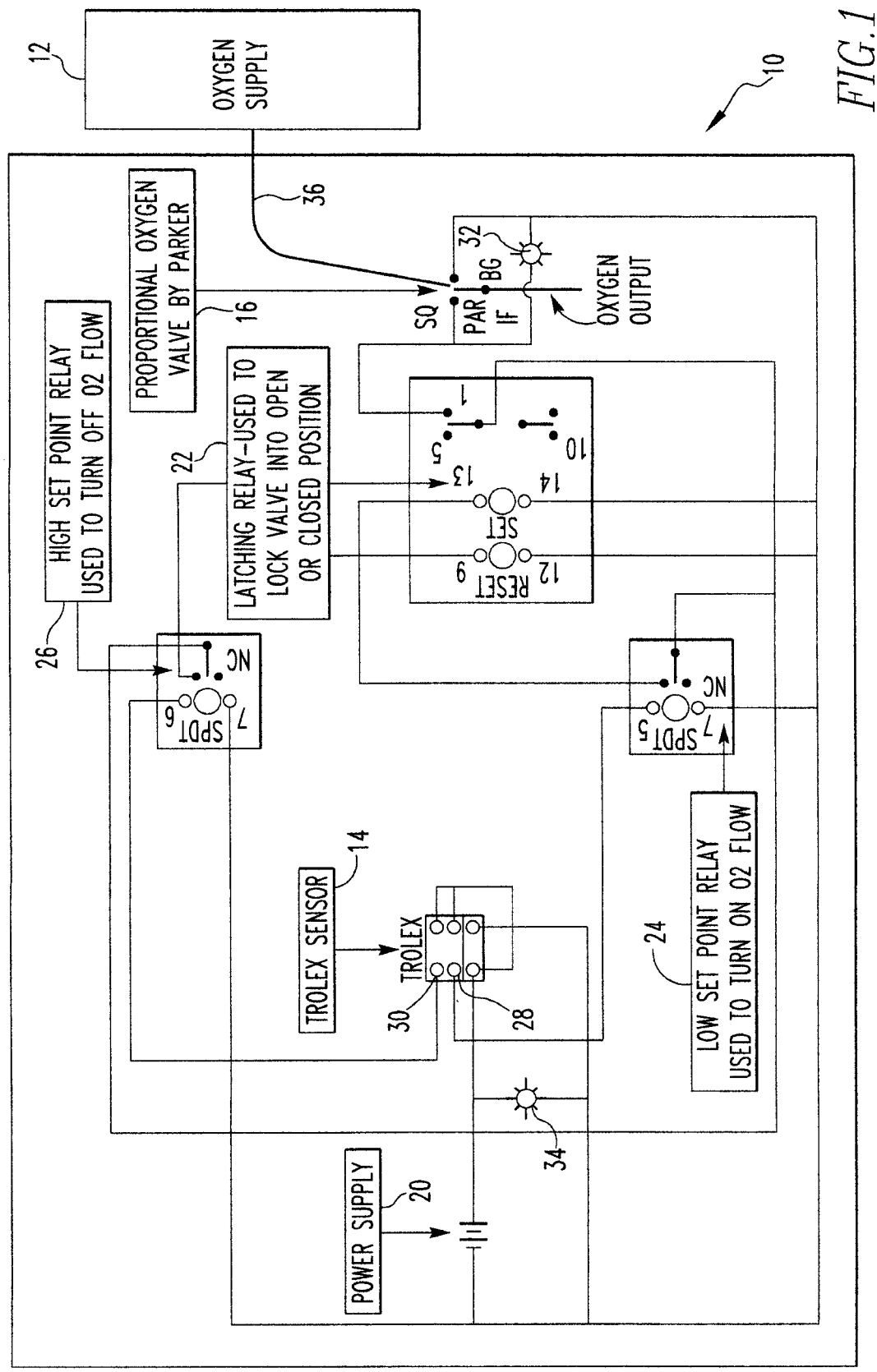
FIG. 1 is a schematic representation of the apparatus of the present invention.
Figure 2:
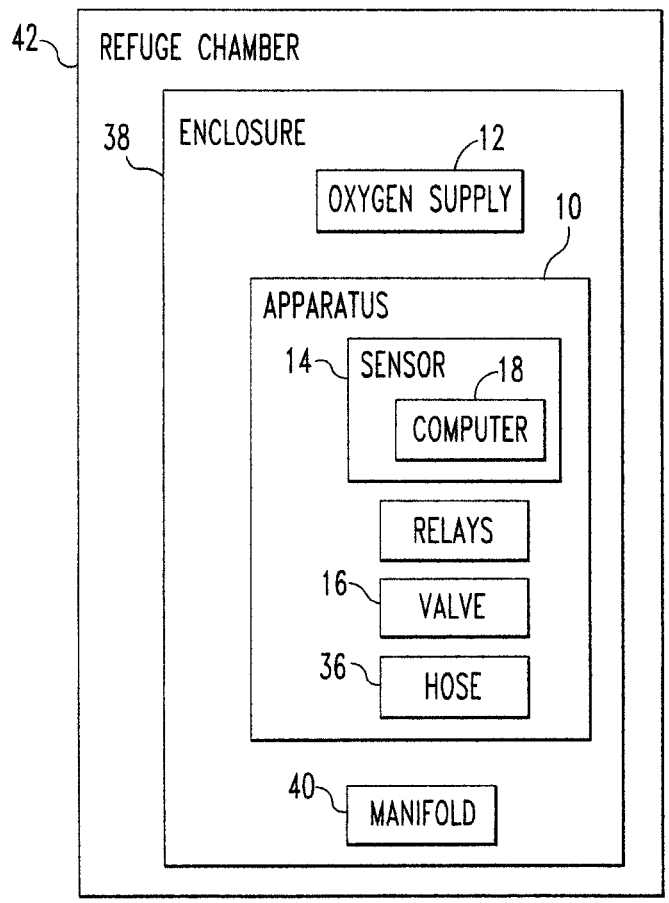
FIG. 2 is a block diagram of a refuge chamber of the present invention.

Referring now to the drawings wherein like reference numerals refer to similar or identical parts throughout the several views, and more specifically to FIGS. 1 and 2 thereof, there is shown an apparatus 10 for controlling a level of oxygen in a closed environment from an oxygen supply 12. The apparatus 10 comprises an oxygen sensor 14 for detecting the level of oxygen in the closed environment. The apparatus 10 comprises a plurality of relays whose operation is controlled by the level of oxygen detected by the sensor 14. The apparatus 10 comprises a valve 16 in communication with the relays and the oxygen supply 12 which is automatically opened by the relays without human interaction, monitoring and adjustment to release oxygen from the oxygen supply 12 into the environment when the level of oxygen in the environment goes below a first predetermined level and which is automatically closed by the relays without human interaction, monitoring and adjustment to stop oxygen from being released from the oxygen supply 12 into the environment when the level of oxygen in the environment goes above a second predetermined level. The refuge may be a safe room or a refuge chamber 42. See U.S. patent application Ser. No. 14/242,502, incorporated by reference herein, for a description of a refuge chamber.

A closed environment can be achieved for instance with a refuge chamber 42 or an enclosure 38 or a room with solid walls that are essentially nonporous so no gases can pass through the enclosure 38 or the walls, or where the enclosure 38 or rooms are formed of a somewhat porous material but there is maintained a positive pressure inside the enclosure 38 for the room relative to outside the enclosure 38 or room so that the atmosphere within the enclosure 38 or room that flows out through the enclosure 38 or the walls due to the positive pressure, effectively isolates the interior of the enclosure 38 or room from the outside environment.

The plurality of relays may include a latching relay 22 connected to the valve 16 and in communication with the sensor 14 which opens the valve 16 after the oxygen level has gone below the first predetermined level and keeps the valve 16 open to release oxygen from the oxygen supply 12 as long as the oxygen level is below the second predetermined level and which closes the valve 16 after the oxygen level has gone above the second predetermined level and keeps the valve 16 closed so no oxygen is released from the oxygen supply 12 as long as the oxygen level is above the first predetermined level. The plurality of relays may include a high side relay 26 in communication with the sensor 14 and the latching relay 22. When the oxygen level is above the second predetermined level the sensor 14 causes a high signal to be sent to the high side relay 26 that activates the high side relay 26 to send a close signal to the latching relay 22 in turn causing the latching relay 22 to close the valve 16. The plurality of relays may include a low side relay 24 in communication with the sensor 14 and the latching relay 22. When the oxygen level is below the first predetermined level, the sensor 14 causes a low signal to be sent to the low side relay 24 that activates the low side relay 24 to send an open signal to the latching relay 22 in turn causing the latching relay 22 to open the valve 16.

The sensor 14 may include a computer 18 which determines whether the oxygen level is above the second predetermined level or below the first predetermined level and causes the high signal or low signal, respectively, to be sent out when appropriate. The apparatus 10 may include a power on light 34 which is lit when the apparatus 10 is on, and an oxygen on light 32 which is lit when oxygen is being released by the valve 16. The apparatus 10 may include a quick release hose 36 connected to the valve 16 and the oxygen supply 12 which can be disengaged from the valve 16 if the valve 16 does not operate.

The present invention pertains to a refuge chamber 42. The refuge chamber 42 comprises an enclosure 38 which provides a protected environment for at least one person to be in. The refuge chamber 42 comprises an oxygen supply 12 in communication with the enclosure 38. The refuge chamber 42 comprises an apparatus 10 disposed in the enclosure 38 for automatically controlling the oxygen level in the enclosure 38 without human interaction, monitoring or adjustment having an oxygen sensor 14, a valve 16 connected to the oxygen supply 12 with a quick release hose 36, and a plurality of relays in communication with the sensor 14 that control when the valve 16 is open or closed regarding release of oxygen by the valve 16 from the oxygen supply 12. The refuge chamber 42 comprises a manifold 40 disposed in the enclosure 38 to which the quick release hose 36 can be connected if the apparatus 10 stops operating so oxygen can continue to be released from the oxygen supply 12. The manifold 40 providing manual control by the person of the oxygen level when the quick release hose 36 is connected to the manifold 40.

The present invention pertains to a method for controlling a level of oxygen in a closed environment from an oxygen supply 12. The method comprises the steps of detecting with an oxygen sensor 14 the level of oxygen in the closed environment is below a first predetermined level. There is the step of automatically opening a plurality of relays whose operations are controlled by the level of oxygen detected by the sensor 14. Without human interaction, monitoring and adjustment a valve 16 which is in communication with the sensor 14 and the oxygen supply 12 to release oxygen from the oxygen supply 12 into the environment. There is the step of detecting with the oxygen sensor 14 the level of oxygen in the closed environment is above a second predetermined level. There is the step of automatically closing with the relays without human interaction, monitoring and adjustment the valve 16 to stop oxygen from being released from the oxygen supply 12 into the environment.

In the operation of the invention, the logic flow of the apparatus 10 is as follows:

The apparatus 10 constantly monitors the O2 level in the atmosphere and is making the following queries:

|  |  |
| --- | --- |
| Is the O2 level below set point "low" --------[ | [no] = no action |
|  | [yes] = open O2 supply valve |
| Is the O2 level above set point "high" -------[ | [no] = no action |
|  | [yes] = close O2 supply valve |

Set point "low" equals the lowest desired atmospheric O2 concentration and set point "high" equals the highest desired atmospheric concentration of O2.

There is an oxygen sensor 14, a computer 18, a 24 v controlling power supply 20, a proportional valve and 3 relays used, two "normally closed" relays (meaning when no current is flowing through the coils, the control contacts remain closed) and one DPDT latching relay 22 (meaning the relay has two controlling coils and if current is applied to coil A the relay "latches" into position A allowing current to flow through side A of the relay contacts). Even if current ceases to flow through side A coils the side A contacts remain closed, "latched" in that position. If current is then subsequently applied to coil B of the latching relay 22, the relay is "latched" in the B position and the B contacts are closed and the relay remains latched to the B side.

There are two "normally closed" contacts in the oxygen sensor 14 that tie to programmable alarms in the sensor 14. A control voltage is applied to a circuit connecting the contacts to the relay coil. As long as the current continues to flow through the sensors closed contacts, the coil, using magnetic force, holds the relay in position in the "not-normal". Since these relays are "normally closed" relays, when the current is flowing through the coil, the relay contacts remain open and no current may flow through the contacts.

If the "low" set point is reached, the oxygen sensor 14 set point "low" contact 28 opens and the voltage through the "low" circuit is interrupted, thus releasing the low side relay 24. Since the low side relay 24 is "normally closed" the voltage interruption allows the contacts of the low side relay 24 to close and current begins flowing through the low side relay 24 contacts to the coil of the "latching" relay and the latching relay 22 is now latched in the position whereby current is allowed to flow to the proportional valve, causing it to open. As soon as the 02 levels increase to the point that the concentration is above the "low" set point, the low side relay 24 contacts reclose allowing current to flow through the coil of the low side relay 24 causing it to abandon its "normal or no current" closed position, opening the low side relay 24 contacts and breaking the current flow to the coil of the latching relay 22. However, since the latching relay 22 is "latched" in the "valve open" position, it will stay in that position, holding open the proportional valve 16 allowing O2 to continue to flow.

The O2 will continue to flow until such time as the O2 concentration reaches the "high" set point. Then the high contact 30 opens interrupting the flow of current to the high side relay 26 allowing the relay to return to the normally closed position. Since the high side relay 26 contacts are closed, current is allowed to flow to the B side of the latching relay 22, "latching" the relay in the "valve closed" position. This causes the valve 16 to close and the O2 flow to cease. As soon as the O2 concentration falls below the high set point, the sensors high set point contact close allowing current to flow to the high side relay 26 coil thus opening the normally closed contacts high side relay 26 and interrupting the flow of current to the B side of the latching relay 22. Again, since it is a latching relay 22, even though the current is no longer flowing through the coil of the B side of the latching relay 22, the latching relay 22 remains latched in the "valve closed" position until the O2 concentration falls enough to trigger the low side alarm of the sensor 14. Then the cycle begins again.

The oxygen sensor 14 and computer 18 may be part of a Trolex gas sensor model Sentro 1 with an Oxygen E Module having part number TX6351.EH or TX6351.01.14. The oxygen sensor 14 in the Trolex senses the oxygen level in the environment. The computer 18 in the Trolex receives the level of oxygen sensed by the sensor 14 and determines if the oxygen level in the environment is above or below predetermined levels. When the oxygen level in the environment is above a predetermined level, a high signal, which would otherwise be sent by the computer 18 to the alarm in the Trolex, is instead sent out of the Trolex to a high side relay 26 to activate the high side relay 26 to cause a latching relay 22 to close the valve 16 and have the valve 16 remain closed, thus stopping any oxygen from the oxygen supply 12 from being released into the environment. When the oxygen level falls below the "high" set point the alarm in the Trolex is deactivated. However, the design of the latching relay 22 continues to keep the valve 16 in the closed position.

When the oxygen level in the environment is below a predetermined level, a low signal, which would otherwise be sent by the computer 18 to the alarm in the Trolex, is instead sent out of the Trolex to a low side relay 24 to activate the low side relay 24 to cause the latching relay 22 to open the valve 16 and have the valve 16 remain open, thus allowing oxygen from the oxygen supply 12 to be released into the environment. When the oxygen exceeds the "low" set point, the alarm is deactivated. However, the design of the latching relay 22 holds the valve 16 in the open position until the "high" alarm is activated.

The effect of this apparatus 10 causes the apparatus 10 to begin delivering O2 when the low set point is reached and discontinuing the flow of O2 when the high set point is reached, keeping the O2 concentration within the desired range.

The apparatus 10 may have a wireless connection to transmit and receive information regarding the oxygen level. See U.S. patent application Ser. No. 14/507,302, incorporated by reference herein, for a description of a wireless communication feature into the apparatus 10.

The purpose of the apparatus 10 is to utilize Trolex Sentro 1 universal gas detector to monitor and maintain the atmospheric levels of oxygen in an enclosed space. The Trolex Sentro 1 "contact output" (TX6351.EH or TX6351.01.14) variant is used. This particular Trolex model has "GENERAL" and "HIGH" alarms and internal relays that allow for 24 VDC that powers the Trolex to be used to power two Omron LY-0-DC24 general purpose relays at two of three possible conditions. The three conditions are:

1. The atmospheric oxygen percentage is less than the desired range
2. The atmospheric oxygen percentage is within the desired range
3. The atmospheric oxygen percentage is more than the desired range Each Omron LY-0-DC24 relay ("Low side relay", "High side relay") operates at mutually exclusive times, and is used to control the voltage (power) to a third relay (latch relay). The third relay is an Omron MY2K-02-DC24 relay. The Omron MY2K-02-DC24 relay is a latching relay 22, meaning that once it is set to one of its positions, it remains in that position until energized to change positions. The two positions for this relay are:

1. The latching relay 22 is affected by the "GENERAL" Trolex alarm, which sets the latching relay 22 to the "on" position, allowing power to flow through to power an external device.
2. The latching relay 22 is affected by the "HIGH" Trolex alarm, which sets the latching relay 22 to the "off" position, stopping the power to an external device.

This latching relay 22 controls the voltage supply to a Parker 920-000047-016 high flow proportional valve 16 as the external device. This valve 16 is a normally closed (NC) valve that requires power to allow gas (oxygen) flow to occur. Because of the use of a latching relay 22 to control the valve 16, the valve 16 will remain open, releasing oxygen, until the "HIGH" Trolex alarm for high oxygen percentage is reached. Once the "HIGH" Trolex alarm is activated, the latching relay 22 is switched to the "off" position, cutting off power to the Parker valve, causing it to close and prevent gas flow. The valve 16 is located in an oxygen line connected to an oxygen supply 12 with oxygen tanks to provide oxygen to the line and ultimately to the closed environment.

System Scenarios and Effects

1. Atmospheric oxygen content is too low
Effects (in order):
A. "GENERAL" Trolex alarm and internal relay are activated
B. 24 VDC is then supplied to the LY-0-DC24 "Low relay"
C. 24 VDC is then supplied to the MY2K-02-DC24 relay, changing it to the "on" position D. 24 VDC is then supplied to the Parker valve, causing it to open E. Oxygen flows from the oxygen supply (pressurized bottle) through the Parker valve and hoses to the atmosphere of the enclosed space 2. Atmospheric oxygen content is too high Effects (in order):

A. "HIGH" Trolex alarm and internal relay are activated

B. 24 VDC is then supplied to the LY-0-DC24 "High relay"

C. 24 VDC is then supplied to the MY2K-02-DC24 relay, changing it to the "off" position D. 24 VDC is then cut off to the Parker valve, causing it to close E. Oxygen flows from the bottle is stopped at the Parker valve In the event of a power failure, the normally closed Parker valve will close, cutting off the supply of oxygen to the enclosed environment atmosphere. The operator of the apparatus 10 would then turn off the regulator for the oxygen supply 12, and use the quick disconnect line on the hose 36 between the oxygen regulator from the high pressure oxygen bottle and the valve control box. After disconnecting the line from the bottle/regulator to the valve 16, the operator would then use the oxygen regulator/bottle combo in the standard manually controlled option to release oxygen.

Operator Information

The apparatus 10 may be in a housing with a blue light 32 and a green light 34. The Trolex is mounted to the housing with the relays and the valve 16 disposed in the housing. The oxygen line extends into the housing to the valve 16 and vents to the closed environment when the valve 16 is open.

The blue light 32 on indicates the Parker valve is open and the apparatus 10 is dispensing oxygen into the air, and is disposed on the electrical wire between the high side relay 26 and the valve 16.

The green light 34 on indicates the apparatus 10 is powered and is disposed on the power line from the power supply 20 to the Trolex.

Figure 3:
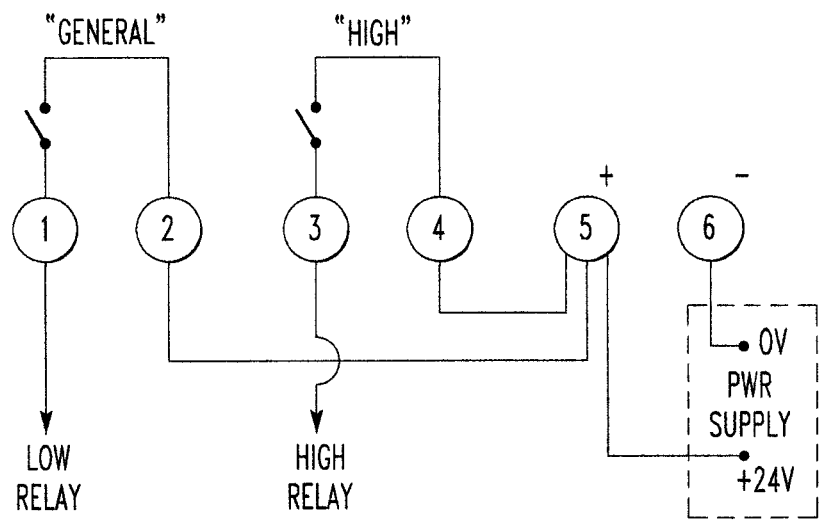
FIG. 3 shows the contact configuration of the Trolex.

FIG. 3 shows the contact setup configuration for the Trolex sensor 14. The Trolex has 6 contacts.

6: negative side of power supply

5: positive side of power supply, jumper to 2 and 4

4: feeds into trolex before trolex internal relay for "high" alarm

3: feeds positive voltage out of trolex when high alarm is on. Does nothing when high alarm is off 2: feeds into trolex before trolex internal relay for "general" alarm 1: feeds positive voltage out of trolex when general (low) alarm is on. Does nothing when general alarm is off.

Essentially, 5 (+) and 6 (−/ground) are incoming power from the power supply. 5 feeds positive voltage to 4 and 2 to the "upside" of the internal Trolex relays. When one of the alarms is set/reached, one of the two internal Trolex relays (depending on the situation) will close, allowing positive voltage through, in turn activating the corresponding (non Trolex internal) non-latching relay 22, which in turn changes/sets the position of the final latching relay 22 that controls the valve 16 for oxygen flow. The relays can be thought of as switches that are opened or closed by some condition. The internal Trolex relays are activated by the Trolex for when either high or general alarms (conditions) are set off/reached. They connect the non-latching relays to the positive voltage as flipping a switch on would.

An example of a first predetermined level regarding the oxygen in the closed environments is under 19%, and for the second predetermined level is over 23%. The Trolex can be set for these thresholds.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

The invention claimed is:

1. An apparatus for controlling a level of oxygen in a closed environment from a pressurized oxygen supply disposed in the closed environment, the apparatus comprising: an oxygen sensor for detecting the level of oxygen in the closed environment; and a plurality of relays whose operation is controlled by the level of oxygen detected by the sensor; and a valve in communication with the plurality of relays and the oxygen supply disposed in the closed environment which is automatically opened by the plurality of relays without human interaction, monitoring or adjustment to release oxygen from the oxygen supply into the closed environment when the level of oxygen in the closed environment goes below a first predetermined level and which is automatically closed by the plurality of relays without human interaction, monitoring and adjustment to stop oxygen from being released from the oxygen supply into the closed environment when the level of oxygen in the closed environment goes above a second predetermined level.

2. The apparatus of claim 1 wherein the plurality of relays include a latching relay connected to the valve and in communication with the sensor which opens the valve after the oxygen level has gone below the first predetermined level and keeps the valve open to release oxygen from the oxygen supply as long as the oxygen level is below the second predetermined level and which closes the valve after the oxygen level has gone above the second predetermined level and keeps the valve closed so no oxygen is released from the oxygen supply as long as the oxygen level is above the first predetermined level.

3. The apparatus of claim 2 wherein the plurality of relays include a high side relay in communication with the sensor and the latching relay, when the oxygen level is above the second predetermined level the sensor causes a high signal to be sent to the high side relay that activates the high side relay to send a close signal to the latching relay in turn causing the latching relay to close the valve; and includes a low side relay in communication with the sensor and the latching relay, when the oxygen level is below the first predetermined level the sensor causes a low signal to be sent to the low side relay that activates the low side relay to send an open signal to the latching relay in turn causing the latching relay to open the valve.

4. The apparatus of claim 3 wherein the sensor includes a computer which determines whether the oxygen level is above the second predetermined level or below the first predetermined level and causes the high signal or low signal, respectively, to be sent out when appropriate.

5. The apparatus of claim 4 including a power-on light which is lit when the apparatus is on, and an oxygen-on light which is lit when oxygen is being released by the valve.

6. The apparatus of claim 5 including a quick release hose connected to the valve and the oxygen supply which is configured to be disengaged from the valve if the valve does not operate.

7. A refuge chamber comprising: an enclosure which provides a protected environment for at least one person to be in; an oxygen supply disposed in the enclosure; an apparatus disposed in the enclosure for automatically controlling an oxygen level in the enclosure without human interaction, monitoring or adjustment having an oxygen sensor, a valve connected to the oxygen supply with a quick release hose, and a plurality of relays in communication with the sensor that control when the valve is open or closed regarding release of oxygen by the valve from the oxygen supply; and a manifold disposed in the enclosure to which the quick release hose is configured to be disconnected if the apparatus stops operating so oxygen is configured to be continually released from the oxygen supply, the manifold providing manual control of the oxygen level when the quick release hose is connected to the manifold.

8. A method for controlling a level of oxygen in a closed environment from an oxygen supply disposed in the closed environment comprising: detecting with an oxygen sensor the level of oxygen in the closed environment is below a first predetermined level; automatically opening with a plurality of relays whose operation is controlled by the level of oxygen detected by the sensor without human interaction, monitoring and adjustment a valve which is in communication with the sensor and the oxygen supply to release oxygen from the oxygen supply into the closed environment; detecting with the oxygen sensor the level of oxygen in the closed environment is above a second predetermined level; and automatically closing with the plurality of relays without human interaction, monitoring and adjustment the valve to stop oxygen from being released from the oxygen supply into the closed environment.

9. The method of claim 8 wherein the plurality of relays include a latching relay connected to the valve and in communication with the sensor which opens the valve after the oxygen level has gone below the first predetermined level and keeps the valve open to release oxygen from the oxygen supply as long as the oxygen level is below the second predetermined level and which closes the valve after the oxygen level has gone above the second predetermined level and keeps the valve closed so no oxygen is released from the oxygen supply as long as the oxygen level is above the first predetermined level.

10. The method of claim 9 wherein the plurality of relays include a high side relay in communication with the sensor and the latching relay, when the oxygen level is above the second predetermined level the sensor causes a high signal to be sent to the high side relay that activates the high side relay to send a close signal to the latching relay in turn causing the latching relay to close the valve; and includes a low side relay in communication with the sensor and the latching relay, when the oxygen level is below the first predetermined level the sensor causes a low signal to be sent to the low side relay that activates the low side relay to send an open signal to the latching relay in turn causing the latching relay to open the valve.

11. The method of claim 10 wherein the sensor includes a computer which determines whether the oxygen level is above the second predetermined level or below the first predetermined level and causes the high signal or low signal, respectively, to be sent out when appropriate.

12. The method of claim 11 including a power-on light which is lit when the apparatus is on, and an oxygen-on light which is lit when oxygen is being released by the valve.

13. The method of claim 12 including a quick release hose connected to the valve and the oxygen supply which is configured to be disengaged from the valve if the valve does not operate.

* * * * *